United States Patent
Katayama et al.

(10) Patent No.: US 11,633,555 B2
(45) Date of Patent: Apr. 25, 2023

(54) NON-COMBUSTION TYPE FLAVOR INHALER AND AEROSOL DELIVERY METHOD

(71) Applicant: JAPAN TOBACCO INC., Tokyo (JP)

(72) Inventors: Kazuhiko Katayama, Tokyo (JP); Akihiko Suzuki, Tokyo (JP); Manabu Takeuchi, Tokyo (JP); Takuma Nakano, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 512 days.

(21) Appl. No.: 15/824,584

(22) Filed: Nov. 28, 2017

(65) Prior Publication Data

US 2018/0077971 A1    Mar. 22, 2018

Related U.S. Application Data

(63) Continuation of application No. PCT/JP2015/065657, filed on May 29, 2015.

(51) Int. Cl.
| | |
|---|---|
| *A24F 40/50* | (2020.01) |
| *A24F 40/10* | (2020.01) |
| *A61M 15/06* | (2006.01) |
| *A61M 11/04* | (2006.01) |
| *F24H 9/20* | (2022.01) |
| *A61M 16/00* | (2006.01) |

(52) U.S. Cl.
CPC ............. *A61M 15/06* (2013.01); *A24F 40/50* (2020.01); *A61M 11/042* (2014.02); *F24H 9/2014* (2013.01); *A24F 40/10* (2020.01); *A61M 2016/0018* (2013.01); *A61M 2205/3653* (2013.01); *A61M 2205/50* (2013.01)

(58) Field of Classification Search
CPC ........ A24F 47/008; A24F 47/00; A24F 40/50; A24F 40/51; A24F 40/53; A24F 40/57
See application file for complete search history.

(56) References Cited

U.S. PATENT DOCUMENTS

| | | |
|---|---|---|
| 10,004,259 B2 | 6/2018 | Sebastian et al. |
| 10,524,512 B2 | 1/2020 | Sebastian et al. |
| 2004/0050383 A1 | 3/2004 | Cox et al. |

(Continued)

FOREIGN PATENT DOCUMENTS

| | | |
|---|---|---|
| CA | 2925647 A1 | 4/2015 |
| CN | 1196660 A | 10/1998 |

(Continued)

OTHER PUBLICATIONS

Japanese Notice of Reasons for Rejection for Japanese Application No. 2018-159197, dated Oct. 2, 2018, with English translation.

(Continued)

*Primary Examiner* — Alex B Efta
(74) *Attorney, Agent, or Firm* — Xsensus LLP

(57) ABSTRACT

A non-combustion type flavor inhaler comprising: an atomizer atomizing an aerosol source without burning; and a controller controlling a power output to the atomizer, wherein the controller is configured to start supply of a power output to the atomizer before start of a user's puffing action, and is configured to stop supply of a power output to the atomizer during a user's puffing action.

16 Claims, 11 Drawing Sheets

(56) References Cited

U.S. PATENT DOCUMENTS

| | | | |
|---|---|---|---|
| 2006/0047368 A1 | 3/2006 | Maharajh et al. | |
| 2006/0201501 A1 | 9/2006 | Morrison et al. | |
| 2010/0242974 A1 | 9/2010 | Pan | |
| 2012/0186594 A1 | 7/2012 | Liu | |
| 2012/0325227 A1 | 12/2012 | Robinson et al. | |
| 2013/0284192 A1* | 10/2013 | Peleg | A24F 40/65 131/329 |
| 2013/0306064 A1* | 11/2013 | Thorens | A24F 40/40 128/202.21 |
| 2013/0319435 A1 | 12/2013 | Flick | |
| 2014/0158129 A1* | 6/2014 | Pratt, Jr. | A61M 16/0078 128/203.26 |
| 2014/0182608 A1 | 7/2014 | Egoyants et al. | |
| 2014/0270727 A1 | 9/2014 | Ampolini et al. | |
| 2014/0299137 A1 | 10/2014 | Kieckbusch et al. | |
| 2014/0299141 A1* | 10/2014 | Flick | H05B 1/0202 219/494 |
| 2014/0321837 A1 | 10/2014 | Flick | |
| 2014/0334804 A1 | 11/2014 | Choi | |
| 2015/0053220 A1* | 2/2015 | Levy | A24F 40/485 131/329 |
| 2015/0128976 A1 | 5/2015 | Verleur et al. | |
| 2015/0181945 A1* | 7/2015 | Tremblay | A24F 47/008 131/328 |
| 2015/0272219 A1 | 10/2015 | Hatrick et al. | |
| 2017/0318861 A1* | 11/2017 | Thorens | A24F 40/53 |
| 2018/0077971 A1 | 3/2018 | Katayama et al. | |
| 2020/0138099 A1 | 5/2020 | Sebastian et al. | |

FOREIGN PATENT DOCUMENTS

| | | |
|---|---|---|
| CN | 102227175 A | 10/2011 |
| CN | 204015092 U | 12/2014 |
| CN | 104540406 A | 4/2015 |
| CN | 104619202 A | 5/2015 |
| EP | 0 845 220 A1 | 6/1998 |
| JP | 11-89551 A | 4/1999 |
| JP | 2000-41654 A | 2/2000 |
| JP | 2002-527153 A | 8/2002 |
| JP | 3325028 B2 | 9/2002 |
| JP | 2010-213579 A | 9/2010 |
| JP | 2011-87569 A | 5/2011 |
| JP | 2012-029633 A | 2/2012 |
| JP | 2014-501107 A | 1/2014 |
| JP | 2014-519850 A | 8/2014 |
| JP | 2014-530632 A | 11/2014 |
| JP | 2014-534814 A | 12/2014 |
| JP | 2015-512262 A | 4/2015 |
| WO | WO 2014/054035 A1 | 4/2014 |
| WO | WO 2014/102091 A1 | 7/2014 |
| WO | WO 2016/194075 A1 | 12/2016 |

OTHER PUBLICATIONS

International Search Report for PCT/JP2015/065657 (PCT/ISA/210) dated Aug. 18, 2015.
Taiwanese Office Action for Application No. 105104723 dispatched on Feb. 21, 2017.
European Search Report dated Oct. 11, 2019, for European Application No. 19180635.5.
Extended European Search Report, dated Oct. 9, 2018, for European Application No. 15894110.4.
European Communication pursuant to Article 94(3) EPC for European Application No. 15894110.4, dated Aug. 9, 2019.
Chinese Office Action and Search Report for Chinese Application No. 201580080175.0, dated Sep. 2, 2019, with partial English translation.
Japanese Office Action for Japanese Application No. 2018-159536, dated Jul. 8, 2019, with English translation.
Office Action dated Jun. 11, 2021 in Japanese Patent Application No. 2021-085573, 5 pages.
Chinese Office Action dated Jan. 29, 2021 issued in corresponding Chinese Patent Application No. 201910140907.0.
Office Action dated Apr. 8, 2022, concerning the corresponding Chinese Patent Application No. 201910675364.2.
Office Action dated Jan. 20, 2023, in Japanese Patent Application No. 2022-103877, 5 pages.

* cited by examiner

NON-COMBUSTION TYPE FLAVOR INHALER AND AEROSOL DELIVERY METHOD

CROSS REFERENCE TO RELATED APPLICATION:

This application is a Continuation of PCT International Application No. PCT/JP2015/065657, filed on May 29, 2015, which is hereby expressly incorporated by reference into the present application.

TECHNICAL FIELD

The present invention relates to a non-combustion type flavor inhaler having an atomizer that atomizes an aerosol source without burning, and an aerosol delivery method.

BACKGROUND ART

Conventionally, a non-combustion type flavor inhaler for inhaling flavor without burning has been known. The non-combustion type flavor inhaler without burning has an atomizer that atomizes an aerosol source without burning, and a sensor that detects a user's puffing action. In accordance with the detection of the puffing action, the non-combustion type flavor inhaler starts supply of a power output to the atomizer (e.g., Patent Literature 1).

CITATION LIST

Patent Literature

Patent Literature 1: JP 11-089551 A

SUMMARY

A first feature is summarized as a non-combustion type flavor inhaler comprising: an atomizer atomizing an aerosol source without burning; and a controller controlling a power output to the atomizer, wherein the controller is configured to start supply of a power output to the atomizer before start of a user's puffing action, and is configured to stop supply of a power output to the atomizer during a user's puffing action.

A second feature is summarized as the non-combustion type flavor inhaler according to the first feature, further comprising an atomization switch that is switched to a state where supply of a power output to the atomizer is stopped when a user's puffing action is performed.

A third feature is summarized as the non-combustion type flavor inhaler according to the second feature, wherein the atomization switch is switched to a state where supply of a power output to the atomizer is started when a user's puffing action is no longer performed.

A fourth feature is summarized as the non-combustion type flavor inhaler according to the second feature or third feature, wherein the atomization switch is linked with a suction sensor that detects a puffing action, and the controller stops supply of a power output to the atomizer when a puffing action is detected by the suction sensor.

A fifth feature is summarized as the non-combustion type flavor inhaler according to any one of the second feature to the fourth feature, wherein the atomization switch is linked with a suction sensor that detects a puffing action, and the controller starts supply of a power output to the atomizer when a puffing action is no longer detected by the suction sensor.

A sixth feature is summarized as the non-combustion type flavor inhaler according to the second feature or the third feature, wherein the atomization switch is linked with a user operation on an operation interface, and the controller stops supply of a power output to the atomizer when a user operation is no longer performed on the operation interface.

A seventh feature is summarized as the non-combustion type flavor inhaler according to any one of the second feature, the third feature and the six feature, wherein the atomization switch is linked with a user operation on an operation interface, and the controller starts supply of a power output to the atomizer when a user operation is performed on the operation interface.

An eighth feature is summarized as the non-combustion type flavor inhaler according to the first feature, further comprising: a first switch that is switched to an ON state when a user operation is being performed on an operation interface, and that is switched to an OFF state when a user operation is not being performed on the operation interface; and a second switch that is switched to an ON state by start of a user's puffing action, and is switched to an OFF state by termination of a user's puffing action, wherein the controller starts supply of a power output to the atomizer when the first switch is switched to the ON state, and the controller stops supply of a power output to the atomizer when the second switch is switched to the ON state.

A ninth feature is summarized as the non-combustion type flavor inhaler according to any one of the first feature to the eighth feature, wherein the controller stops supply of a power output to the atomizer when a first duration has elapsed after starting of supply of a power output to the atomizer.

A tenth feature is summarized as the non-combustion type flavor inhaler according to the ninth feature, wherein the controller restarts supply of a power output to the atomizer when a second duration has elapsed after stopping of the supply of a power output to the atomizer due to the elapse of the first duration.

An eleventh feature is summarized as the non-combustion type flavor inhaler according to any one of the first feature to the tenth feature, further comprising a notification unit for notifying that a desired amount of aerosol can be supplied, in a period in which the desired amount of aerosol can be supplied.

A twelfth feature is summarized as the non-combustion type flavor inhaler according to any one of the first feature to the eleventh feature, further comprising: a notification unit that notifies that a desired amount of aerosol cannot be supplied in a period in which the desired amount of aerosol cannot be supplied.

A thirteenth feature is summarized as the non-combustion type flavor inhaler according to any one of the first feature to the twelfth feature, wherein an absorbing member for absorbing a condensed aerosol is provided on a wall surface exposed to a flow path of aerosol generated by the atomizer.

A fourteenth feature is summarized as the non-combustion type flavor inhaler according to any one of the first feature to the thirteenth feature, further comprising: a suction sensor that detects a puffing action, wherein the controller triggers energization processing for the atomizer when switching is performed from a non-suction state in which a puffing action is not detected by the suction sensor, to a suction state in which a puffing action is detected by the suction sensor, and from the suction state to the non-suction state.

A fifteenth feature is summarized as an aerosol delivery method comprising: a step A of generating aerosol in a suction path continuing from an inlet to an outlet, in a state in which no fluid flow occurs in the suction path; and a step B of transferring the aerosol into a user's mouth with a fluid flow in the suction path in a state in which generation of the aerosol is stopped after the step A.

A sixteenth feature is summarized as the aerosol delivery method according to the thirteenth feature, wherein the step A is a step of starting supply of a power output to an atomizer when a user operation is performed on an operation interface, and the step B is a step of stopping supply of a power output to the atomizer when a user operation is no longer performed on the operation interface.

It should be noted that, in the above described features, the user operation on the operation interface does not include a user's puffing action. The operation interface is not particularly limited, but is an interface that is directly operated by a user's hand or the like. The user operation on the operation interface is, for example, a button operation, a lever operation, a switch operation, or the like.

DESCRIPTION OF EMBODIMENTS

Figure 1:
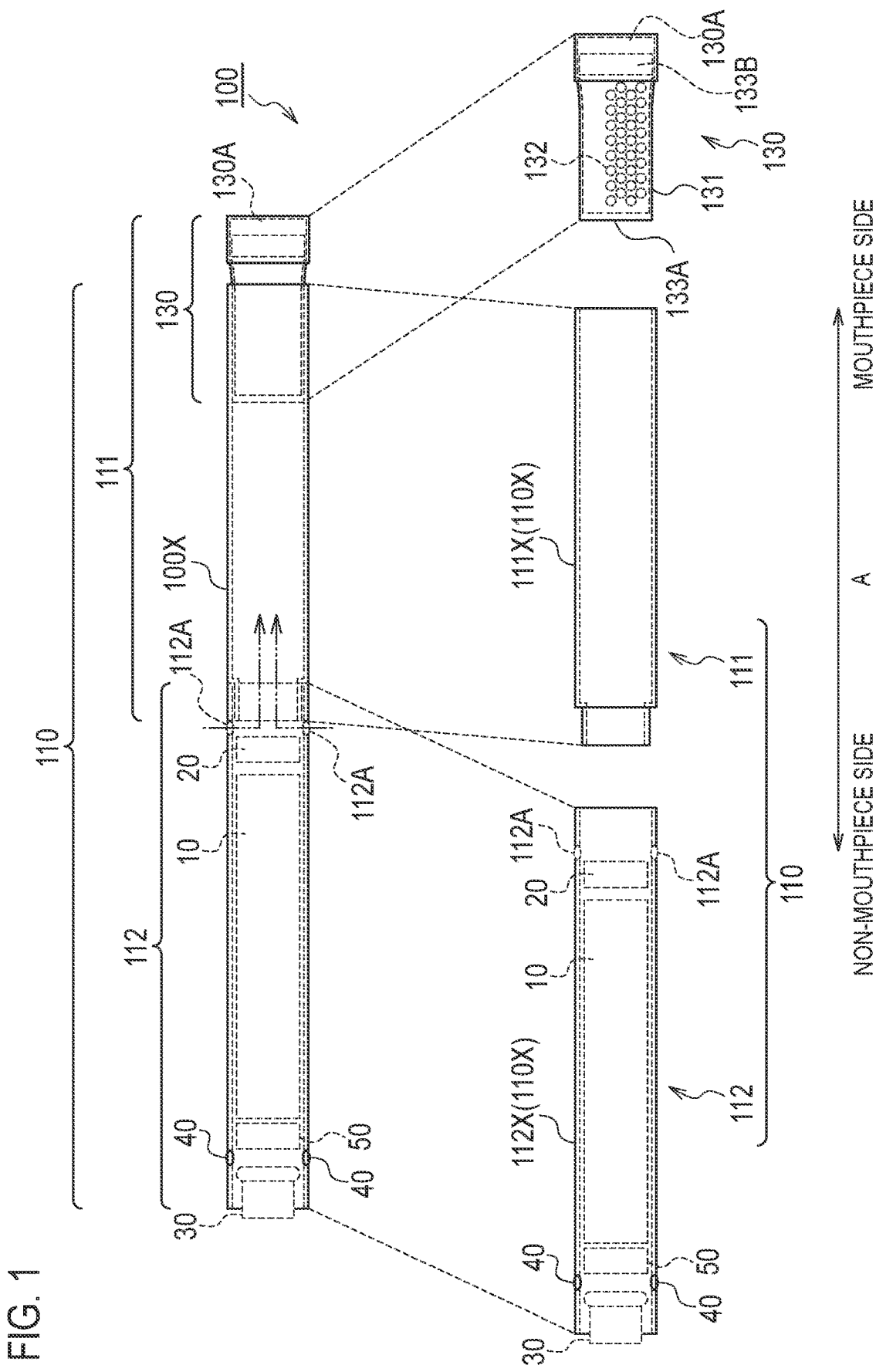
FIG. 1 is a view showing a flavor inhaler 100 according to an embodiment.

Hereinafter, the embodiments of the present invention will be described with reference to the drawings. In the following drawings, identical or similar components are denoted by identical or similar reference numerals.

Therefore, specific dimensions should be determined with reference to the description below. It is needless to mention that different relationships and ratio of dimensions may be included in different drawings.

[Summary of Embodiment]

In accordance with the detection of the puffing action, the non-combustion type flavor inhaler described in the above background art starts supply of the power output to the atomizer. However, since temperature of the atomizer changes during the generation of the aerosol by the atomizer, a particle diameter distribution of particles constituting the aerosol is spread. In other words, the particle diameter of the particles constituting the aerosol varies within one puffing action or among a plurality of puffing actions.

A non-combustion type flavor inhaler according to an embodiment includes an atomizer that atomizes an aerosol source without burning, and a controller that controls a power output to the atomizer. The controller starts supply of the power output to the atomizer before start of a user's puffing action, and stops the supply of the power output to the atomizer during the user's puffing action.

In the embodiment, the controller stops supply of the power output to the atomizer during a user's puffing action. During generation of aerosol by the atomizer, temperature of the atomizer is not changed by the user's puffing action. This prevents a particle diameter of particles constituting aerosol from varying within one puffing action or among a plurality of puffing actions.

[Embodiment]

(Non-Combustion Type Flavor Inhaler)

Figure 2:
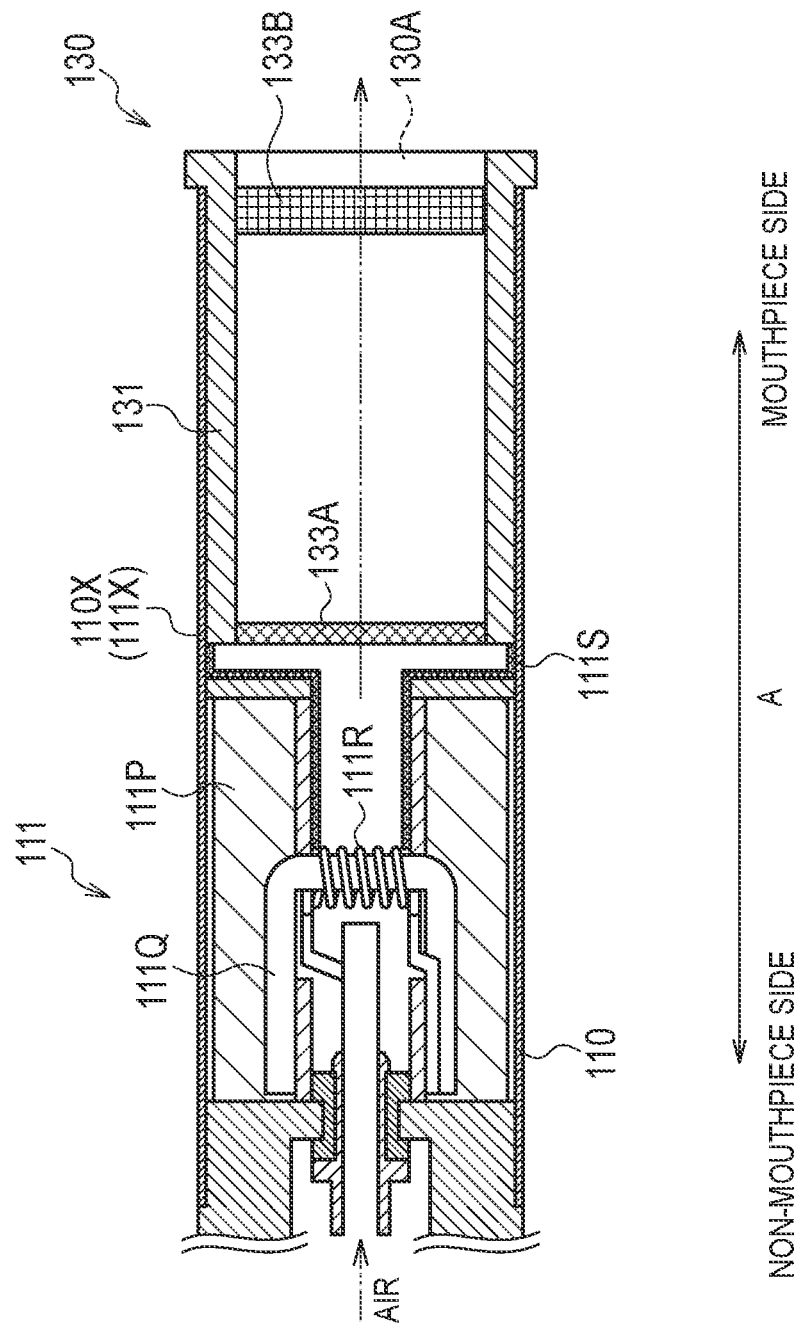
FIG. 2 is a view showing an atomizing unit 111 according to the embodiment.

Hereinafter, non-combustion type flavor inhaler according to an embodiment will be described. FIG. 1 is a view showing a non-combustion type flavor inhaler 100 according to the embodiment. The non-combustion type flavor inhaler 100 is a device for inhaling a flavoring component without burning, and has a shape extending along a predetermined direction A that is a direction from a non-inhalation end toward an inhalation end. FIG. 2 is a view showing an atomizing unit 111 according to the embodiment. It should be noted that, in the following description, the non-combustion type flavor inhaler 100 is simply referred to as a flavor inhaler 100.

As shown in FIG. 1, the flavor inhaler 100 has an inhaler body 110 and a cartridge 130.

The inhaler body 110 forms a main body of the flavor inhaler 100, and has a shape connectable with the cartridge 130. Specifically, the inhaler body 110 has an inhaler housing 110X, and the cartridge 130 is connected to an inhalation end of the inhaler housing 110X. The inhaler body 110 has the atomizing unit 111 configured to atomize the aerosol source without burning, and an electrical unit 112.

In the embodiment, the atomizing unit 111 has a first cylinder 111X forming a part of the inhaler housing 110X. As shown in FIG. 2, the atomizing unit 111 has a reservoir 111P, a wick 111Q, and an atomizer 111R. The reservoir 111P, the wick 111Q, and the atomizer 111R are accommodated in the first cylinder 111X. The first cylinder 111X has a tubular shape (e.g., cylindrical shape) extending along the predetermined direction A. The reservoir 111P holds the aerosol source. For example, the reservoir 111P may be a porous body made of a material such as a resin web. The wick 111Q is an example of a liquid holding member that holds the aerosol source supplied from the reservoir 111P. For example, the wick 111Q is made of glass fiber. The atomizer 111R atomizes the aerosol source held by the wick 111Q. The atomizer 111R is configured by, for example, a heating resistor (e.g., a heating wire) wound around the wick 111Q at a predetermined pitch.

The aerosol source is liquid such as propylene glycol or glycerin. The aerosol source is held, for example, by a porous body made of a material such as a resin web as described above. The porous body may be made of a non-tobacco material, or may be made of a tobacco material. The aerosol source may contain a flavoring component (e.g., a nicotine component or the like). Alternatively, the aerosol source may not contain the flavoring component.

In the embodiment, on a wall surface exposed to a flow path of aerosol generated by the atomizer 111R, there is provided an absorbing member 111S that absorbs condensed aerosol. The wall surface exposed to the flow path of aerosol is, for example, an inner surface of the first cylinder 111X exposed to the flow path of aerosol, an outer surface of the reservoir 111P exposed to the flow path of aerosol, and the like. Here, when the absorbing member 111S is not in contact with the reservoir 111P, the aerosol (condensed aerosol) absorbed by the absorbing member 111S is preferably guided from the absorbing member 111S to the atomizer 111R by utilizing a capillary phenomenon. On the other hand, when the absorbing member 111S is in contact with the reservoir 111P, the aerosol (condensed aerosol) absorbed by the absorbing member 111S is preferably guided from the absorbing member 111S to the reservoir 111P. The absorbing member 111S only needs to be a member having a function of absorbing the condensed aerosol. For example, the absorbing member 111S may be made of a same material as that of the reservoir 111P (resin web), and may also be made of a same material as that of the wick 111Q (glass fiber).

The electrical unit 112 has a second cylinder 112X forming a part of the inhaler housing 110X. In the embodiment, the electrical unit 112 has an inlet 112A. As shown in FIG. 2, air flowing in from the inlet 112A is guided to the atomizing unit 111 (atomizer 111R). Specifically, the electrical unit 112 has a power source 10, a suction sensor 20, a pushbutton 30, a light-emitting element 40, and a control circuit 50. The power source 10, the suction sensor 20, the pushbutton 30, and the control circuit 50 are accommodated in the second cylinder 112X. The second cylinder 112X has a tubular shape (e.g., cylindrical shape) extending along the predetermined direction A.

The power source 10 is a lithium-ion battery, for example. The power source 10 accumulates electric power required for operating the flavor inhaler 100. For example, the power source 10 accumulates electric power to be supplied to the suction sensor 20 and the control circuit 50. Further, the power source 10 accumulates electric power to be supplied to the atomizing unit 111 (atomizer 111R).

The suction sensor 20 detects a fluid flow in a suction path continuing from the inlet 112A to an outlet 130A. The suction sensor 20 detects a suction (suction state) when the fluid flow from the inlet 112A to the outlet 130A side is equal to or higher than a predetermined threshold value. The suction sensor 20 detects a non-suction (non-suction state) when the fluid flow from the inlet 112A to the outlet 130A side is less than the predetermined threshold value.

The pushbutton 30 is configured to be pushed inward from outside of the flavor inhaler 100. In the embodiment, the pushbutton 30 is provided at the non-inhalation end of the flavor inhaler 100, and configured to be pushed in a direction from the non-inhalation end toward the inhalation end (i.e. in the predetermined direction A). For example, in a state where the flavor inhaler 100 is not powered on, when the pushbutton 30 is continuously pushed in for a predetermined number of times, the flavor inhaler 100 may be powered on. On the other hand, in a state where the flavor inhaler 100 is powered on, when the pushbutton 30 is continuously pushed in for a predetermined number of times, the flavor inhaler 100 may be powered off Alternatively, the flavor inhaler 100 may be powered off when a predetermined time elapses without a puffing action after a puffing action is performed.

The light-emitting element 40 is, for example, a light source such as an LED or an electric lamp. The light-emitting element 40 is provided on a sidewall extending along a predetermined direction. The light-emitting element 40 is preferably provided on a side wall near the non-inhalation end. This allows a user to visually recognize a light-emitting pattern of the light-emitting element 40 easily during a puffing action, as compared with a case where the light-emitting element is provided only on an end face of the non-inhalation end on an axis in the predetermined direction A. The light-emitting pattern of the light-emitting element 40 is a pattern to notify a user of a state of the flavor inhaler 100.

In the embodiment, the light-emitting element 40 may form a notification unit to notify that a desired amount of aerosol can be supplied. Here, the light-emitting element 40 may continuously notify that the desired amount of aerosol can be supplied, from start to end of a period in which the desired amount of aerosol can be supplied. Alternatively, the light-emitting element 40 may form a notification unit to notify that the desired amount of aerosol cannot be supplied. Here, the light-emitting element 40 may continuously notify that the desired amount of aerosol cannot be supplied, from start to end of a period in which the desired amount of aerosol cannot be supplied.

The control circuit 50 controls operation of the flavor inhaler 100. Specifically, the control circuit 50 controls the power output to the atomizing unit 111 (atomizer 111R). Further, the control circuit 50 controls the light-emitting element 40.

The cartridge 130 is configured to be connectable to the inhaler body 110 foaming the flavor inhaler 100. The cartridge 130 is provided on a downstream side of the atomizing unit 111 on a flow path of gas (hereinafter, air) inhaled from an inhalation port. In other words, the cartridge 130 is not necessarily provided on an inhalation side from the atomizing unit 111 in terms of a physical space, as long as the cartridge 130 is provided on the downstream side of the atomizing unit 111 on the aerosol flow path for guiding aerosol generated from the atomizing unit 111.

Specifically, the cartridge 130 has a cartridge housing 131, a flavor source 132, a mesh 133A, and a filter 133B. Further, the cartridge 130 has the outlet 130A provided at the inhalation port.

The cartridge housing 131 has a tubular shape (e.g., cylindrical shape) extending along the predetermined direction A. The cartridge housing 131 accommodates the flavor source 132. Here, the cartridge housing 131 is configured to be inserted into the inhaler housing 110X along the predetermined direction A.

The flavor source 132 is provided closer to the outlet 130A (inhalation port) than the atomizing unit 111 on the suction path continuing from the inlet 112A to the outlet 130A. The flavor source 132 gives a flavoring component to aerosol generated from the aerosol source. In other words, the flavoring component given to the aerosol by the flavor source 132 is conveyed to the outlet 130A (inhalation port).

In the embodiment, the flavor source 132 is made by a raw material piece that gives the flavoring component to aerosol generated from the atomizing unit 111. A size of the raw material piece is preferably 0.2 mm or more to 1.2 mm or less. Further, the size of the raw material piece is preferably 0.2 mm or more to 0.7 mm or less. Since a specific surface area is increased as the size of the raw material piece composing the flavor source 132 is smaller, the flavoring component is easily released from the raw material piece composing the flavor source 132. Therefore, in giving a desired amount of the flavoring component to aerosol, an amount of the raw material piece can be suppressed. As the raw material piece composing the flavor source 132, it is possible to use a shredded tobacco, and a molded body of a granulated tobacco material. However, the flavor source 132 may be a molded body formed into a sheet tobacco material. Further, the raw material piece composing the flavor source 132 may be composed of a plant other than tobacco (e.g., mint, herbs, and the like). The flavor source 132 may be given flavors such as menthol.

Here, the raw material piece composing the flavor source 132 is obtained by sieving according to JIS Z 8815, for example, by using a stainless steel sieve according to JIS Z 8801. For example, by using a stainless steel sieve having a mesh opening of 0.71 mm, the raw material pieces are sieved for 20 minutes by a dry type mechanical shaking method, providing raw material pieces passing through the stainless steel sieve having the mesh opening of 0.71 mm. Subsequently, by using a stainless steel sieve having a mesh opening of 0.212 mm, the raw material pieces are sieved for 20 minutes by a dry type mechanical shaking method, removing the raw material pieces passing through the stainless steel sieve having the mesh opening of 0.212 mm. That is, the raw material piece composing the flavor source 132 is a raw material piece that passes through the stainless steel sieve (mesh opening=0.71 mm) defining an upper limit, but does not pass through the stainless steel sieve (mesh opening=0.212 mm) defining a lower limit. Accordingly, in the embodiment, the lower limit of the size of the raw material piece composing the flavor source 132 is defined by the mesh opening of the stainless steel sieve defining the lower limit. Moreover, the upper limit of the size of the raw material piece composing the flavor source 132 is defined by the mesh opening of the stainless steel sieve defining the upper limit.

In the embodiment, the flavor source 132 is a tobacco source having an alkaline pH. A pH of the tobacco source is preferably greater than 7, and more preferably 8 or more. Setting the pH greater than 7 makes it possible to efficiently take out the flavoring component generated from the tobacco source, by aerosol. This can suppress the amount of the tobacco source in giving a desired amount of the flavoring component to aerosol. On the other hand, the pH of the tobacco source is preferably 12 or less, and more preferably 10 or less. Setting the pH to 12 or less can more effectively prevent damage (such as corrosion) to the flavor inhaler 100 (e.g., the cartridge 130 or the inhaler body 110).

It should be noted that the flavoring component generated from the flavor source 132 is conveyed by aerosol, and the flavor source 132 itself does not need to be heated.

The mesh 133A is provided so as to close an opening of the cartridge housing 131 on upstream of the flavor source 132, and the filter 133B is provided so as to close the opening of the cartridge housing 131 on downstream of the flavor source 132. The mesh 133A has roughness of a degree not to be passed by the raw material piece composing the flavor source 132. The roughness of the mesh 133A has a mesh opening of, for example, 0.077 mm or more to 0.198 mm or less. The filter 133B is made of a permeable material. The filter 133B is preferably an acetate filter, for example. The filter 133B has roughness of a degree not to be passed by the raw material piece composing the flavor source 132.

(Block Configuration)

Figure 3:
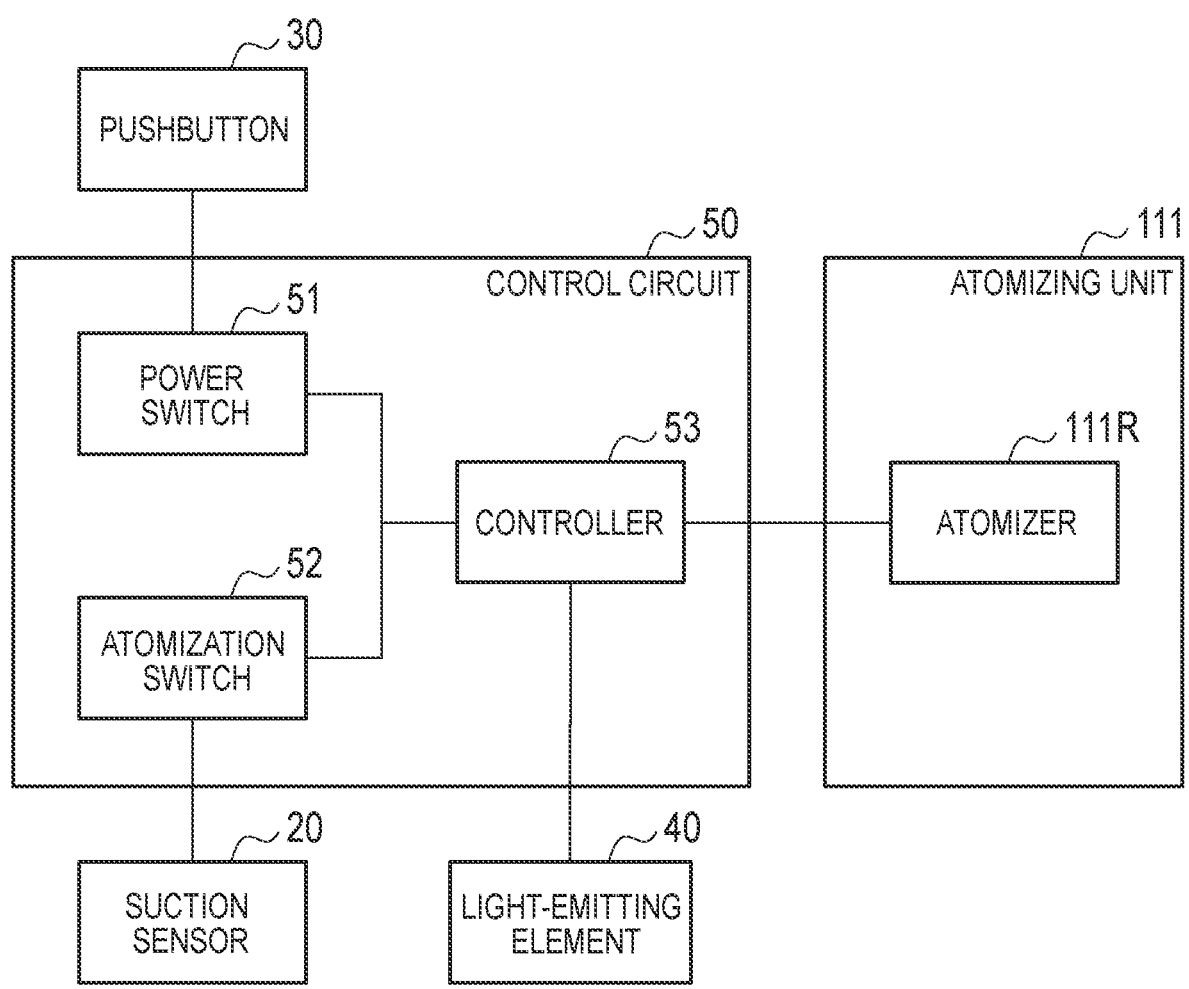
FIG. 3 is a diagram showing a block configuration of the flavor inhaler 100 according the embodiment.

Hereinafter, a block configuration of the non-combustion type flavor inhaler according to the embodiment will be described. FIG. 3 is a diagram showing a block configuration of the flavor inhaler 100 according to the embodiment.

As shown in FIG. 3, the control circuit 50 has a power switch 51, an atomization switch 52, and a controller 53.

The power switch 51 is switched to an ON state when the flavor inhaler 100 is powered on, and switched to an OFF state when the flavor inhaler 100 is powered off. For example, the power switch 51 may be connected to the pushbutton 30, and may be switched to the ON state when the pushbutton .30 is continuously pushed in for a predetermined number of times, in a state where the flavor inhaler 100 is not powered on. On the other hand, the power switch 51 may be switched to the OFF state when the pushbutton 30 is continuously pushed in for a predetermined number of times, in a state where the flavor inhaler 100 is powered on. Alternatively, the power switch 51 may have a timer to be activated in response to termination of a puffing action, and may be switched to the OFF state in response to expiration of the timer (elapse of a predetermined time).

When a user's puffing action is performed, the atomization switch 52 is switched to a state (OFF state) where supply of the power output to the atomizer 111R is stopped, and when the user's puffing action is no longer performed, the atomization switch 52 is switched to a state (ON state) where supply of the power output to the atomizer 111R is started. In the embodiment, the atomization switch 52 is linked with the suction sensor that detects a puffing action. The atomization switch 52 is switched to the OFF state when a puffing action is detected by the suction sensor 20. On the other hand, the atomization switch 52 is switched to the ON state when the puffing action is no longer detected by the suction sensor 20.

Here, a state where the puffing action is not detected by the suction sensor 20 is also referred to as the non-suction state, and a state where a puffing action is detected by the suction sensor 20 is also referred to as the suction state. Therefore, the atomization switch 52 is switched to the OFF state by switching from the non-suction state to the suction state, and switched to the ON state by switching from the suction state to the non-suction state.

The controller 53 controls the flavor inhaler 100 in a state where the flavor inhaler 100 is powered on.

First, the controller 53 controls a power output to the atomizer 111R. In the embodiment, the controller 53 starts supply of the power output to the atomizer 111R before the start of the user's puffing action, and stops the supply of the power output to the atomizer 111R during the user's puffing action. In the embodiment, when the atomization switch 52 is turned off, the controller 53 stops the supply of the power output to the atomizer 111R. On the other hand, when the atomization switch 52 is turned on, the controller 53 starts the supply of the power output to the atomizer 111R. In other words, when a puffing action is detected by the suction sensor 20, the controller 53 stops the supply of the power output to the atomizer 111R. On the other hand, when the puffing action is no longer detected by the suction sensor 20, the controller 53 starts the supply of the power output to the atomizer 111R.

Here, in a case where a voltage is continuously applied to the atomizer 111R, magnitude of the power output is defined by a value of the voltage applied to the atomizer 111R. On the other hand, in a case where the voltage is intermittently applied to the atomizer 1I1R (pulse control), the magnitude of the power output is defined by at least any one of parameters of the value of the voltage applied to the atomizer 111R, a pulse width, and a pulse interval.

In the embodiment, when a first duration has elapsed after starting of supply of the power output to the atomizer 111R, the controller 53 may stop the supply of the power output to the atomizer 111B. Here, the first duration is a time for keeping a supply amount of aerosol within a desired amount without depending on a time length of the non-suction state. In other words, the first duration is a time determined to prevent the supply amount of aerosol from exceeding an upper limit of the desired amount range.

For example, an upper limit of the first duration is preferably 5 seconds. More preferably, the upper limit of the first duration is 4 seconds, and even more preferably the upper limit of the first duration is 3 seconds. For example, a lower limit of the first duration is preferably 0.5 seconds. More preferably, the lower limit of the first duration is 1 second, and even more preferably the lower limit of the first duration is 1.5 seconds. For example, the first duration is preferably 0.5 seconds or more to 5 seconds or less. More preferably, the first duration is 1 second or more to 4 seconds or less. Even more preferably, the first duration is preferably 1.5 seconds or more to 3 seconds or less.

In the embodiment, when a second duration has elapsed after stopping of the supply of the power output to the atomizer 111R due to elapse of the first duration, the controller 53 may restart the supply of the power output to the atomizer 111R. Here, the second duration is a time determined to prevent the supply amount of aerosol from falling below a lower limit of the desired amount range due to condensation of aerosol on the wall surface exposed to the flow path of aerosol. The condensed aerosol absorbed by the absorbing member 111S may be re-atomized by restarting supply of the power output.

As described above, when the absorbing member 111S is not in contact with the reservoir 111P, the aerosol (condensed aerosol) absorbed by the absorbing member 111S is preferably guided from the absorbing member 111S to the atomizer 111R by utilizing a capillary phenomenon. On the other hand, when the absorbing member 111S is in contact with the reservoir 111P, the aerosol (condensed aerosol) absorbed by the absorbing member 111S is preferably guided from the absorbing member 111S to the reservoir 111P.

Secondly, the controller 53 controls the light-emitting element 40. In the embodiment, the controller 53 may control the light-emitting element 40 to notify that a desired amount of aerosol can be supplied. The controller 53 may control the light-emitting element 40 to continuously notify that the desired amount of aerosol can be supplied, from start to end of a period in which the desired amount of aerosol can be supplied. For example, a start timing of the period in which the desired amount of aerosol can be supplied is a timing at which a certain time shorter than the first duration has elapsed after starting of supply of the power output to the atomizer 111R. The certain time is, for example, a time from starting of supply of the power output to the atomizer 111R until the supply amount of aerosol reaches the lower limit of the desired amount range.

Further, the controller 53 may control the light-emitting element 40 to notify that the desired amount of aerosol cannot be supplied. The controller 53 may control the light-emitting element 40 to continuously notify that the desired amount of aerosol cannot be supplied, from start to end of a period in which the desired amount of aerosol cannot be supplied. A start timing of the period in which the desired amount of aerosol cannot be supplied is, for example, a timing at which supply of the power output to the atomizer 111R is started. An end timing of the period in which the desired amount of aerosol cannot be supplied is similar to the start timing of the period in which the desired amount of aerosol can be supplied.

Thirdly, the controller 53 may trigger energization processing for the atomizer 111R when the non-suction state is switched to the suction state, and the suction state is switched to the non-suction state. In other words, an initial puffing action is performed to trigger the energization processing for the atomizer 111R without generation of aerosol. The energization processing for the atomizer 111R is processing of generating aerosol by supplying the power output to the atomizer 111R.

For example, the initial puffing action may be used to authenticate whether the user is an authorized user. For example, when the response value of the suction sensor 20 associated with the initial puffing action satisfies a predetermined condition (e.g., a condition that a slope of a flow rate is equal to or more than a predetermined value), the user is authenticated as an authorized user. The initial puffing action may be an initial puffing action after introducing of the power supply of the flavor inhaler 100, or may be an initial puffing action after a predetermined time has elapsed without a puffing action performed. Here, if switching from the non-suction state to the suction state and switching from the suction state to the non-suction state are not performed within a trigger time for the initial puffing action, the controller 53 may not trigger the energization processing for the atomizer 111R. For such an authentication operation, the whole contents of International Application No. PCT/JP2015/63036 (filed Apr. 30, 2015) is incorporated by reference.

(Example of Control)

Hereinafter, an example of control of the power output to the atomizer 111R according to embodiment will be described. FIG. 4 is a graph for explaining an example of control of the power output to the atomizer 111R according to the embodiment.

As described above, the controller 53 starts supply of the power output to the atomizer 111R when the atomization switch 52 is turned on (i.e., the non-suction state). The controller 53 stops supply of the power output to the atomizer 111R when the atomization switch 52 is turned off (i.e., the suction state).

In such a case, as shown in FIG. 4, the controller 53 stops supply of the power output to the atomizer 111R when the first duration elapses with the atomization switch 52 being in the ON state (i.e., the non-suction state) after starting of supply of the power output to the atomizer 111R. The first duration is a time determined to prevent the supply amount of aerosol from exceeding the upper limit of the desired amount range. The first duration is variable depending on the amount of aerosol staying in the aerosol flow path.

In addition, after stopping of supply of the power output to the atomizer 111R due to elapse of the first duration, the controller 53 restarts the supply of the power output to the atomizer 111R when the second duration elapses with the atomization switch 52 being in the ON state (i.e., the non-suction state). The second duration is a time determined to prevent the supply amount of aerosol from falling below the lower limit of the desired amount range. In the example of control according to the embodiment, by repeatedly stopping and restarting the supply of the power output to the atomizer 111R, the supply amount of aerosol increases or decreases within the desired amount range. Here, while the desired amount range may be determined by the upper limit and the lower limit, the lower limit is preferably 0.1 mg or more, and more preferably 1.0 mg or more. On the other hand, the upper limit of the desired amount is preferably 10.0 mg or less, and more preferably 5.0 mg or less. The desired amount range may be 0.1 mg or more to 10.0 mg or less, or may be 1.0 mg or more to 5.0 mg or less. The desired amount range may be determined based on a target value of the desired amount. For example, based on the target value of the desired amount, the desired amount range is preferably a range of ±50% or less (e.g., when the target value of the desired amount is 2.0 mg, the desired amount range is 1.0 mg or more to 3.0 mg or less), and more preferably a range of ±25% or less (e.g., when the target value of the desired amount is 2.0 mg, the desired amount range is 1.5 mg or more to 2.5 mg or less).

Here, the controller 53 controls the light-emitting element 40 to notify that the desired amount of aerosol can be supplied. Further, the controller 53 controls the light-emitting element 40 to notify that the desired amount of aerosol cannot be supplied. In the example of control according to the embodiment, it is notified that the desired amount of aerosol cannot be supplied, after starting of supply of the power output to the atomizer 111R until the supply amount of aerosol reaches the lower limit of the desired amount range. When the supply amount of aerosol exceeds the lower limit of the desired amount range after starting of supply of the power output to the atomizer 111R, it is notified that the desired amount of aerosol can be supplied. The start timing of the period in which the desired amount of aerosol can be supplied is a timing at which a certain time shorter than the first duration has elapsed after starting of supply of the power output to the atomizer 111R. The certain time is, for example, a time from starting of supply of the power output to the atomizer 111R until the supply amount of aerosol reaches the lower limit of the desired amount range.

(Aerosol Delivery Method)

Figure 5:
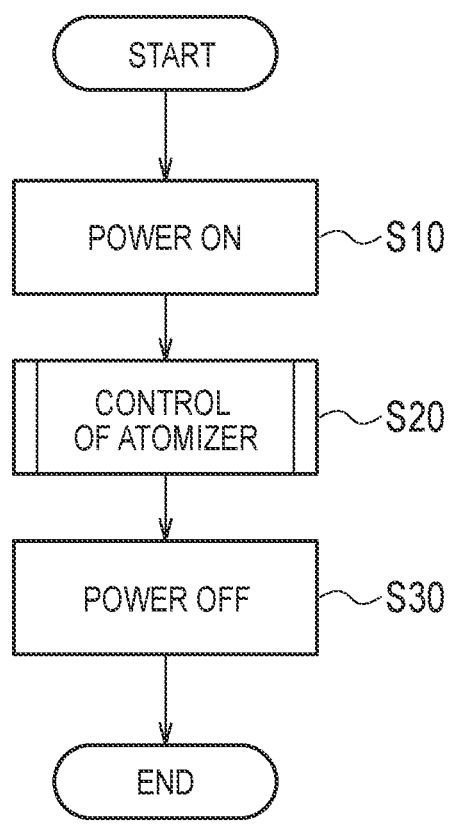
FIG. 5 is a flowchart showing an aerosol delivery method according to the embodiment.
Figure 6:
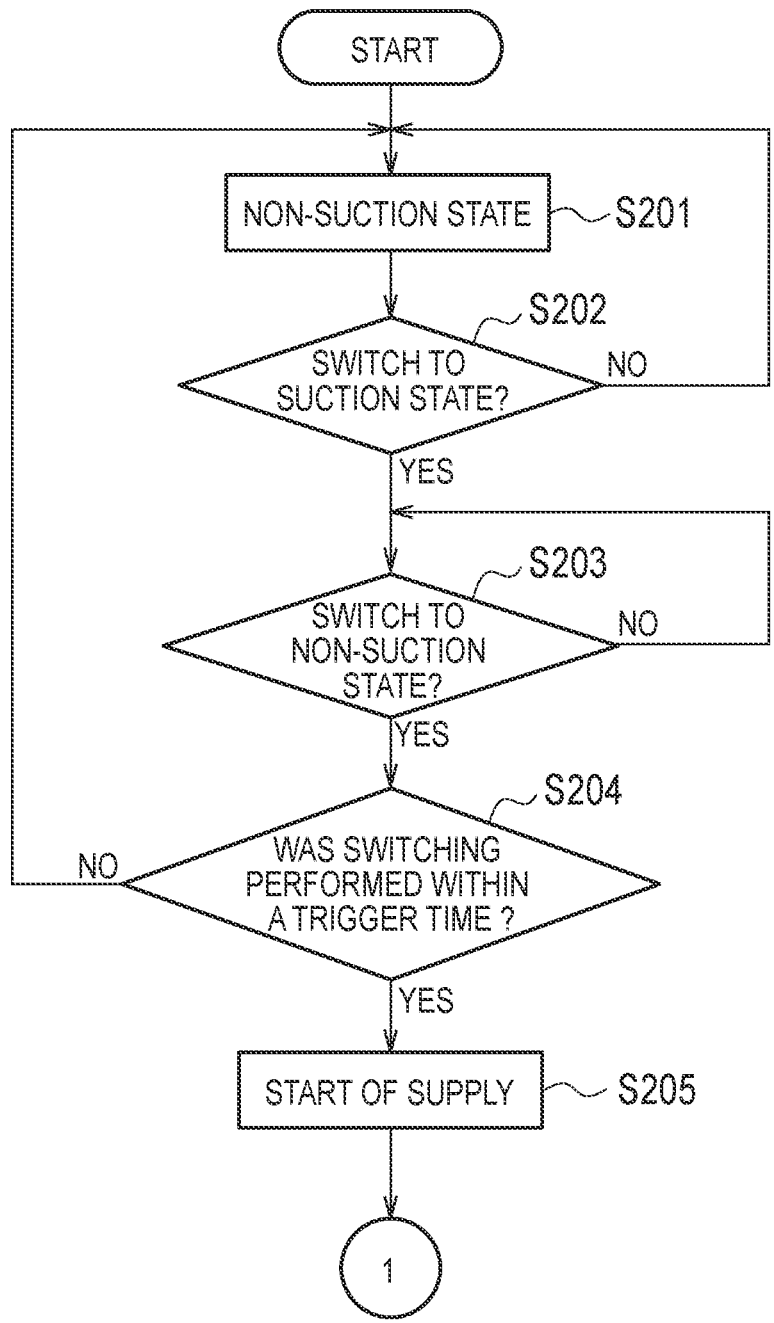
FIG. 6 is a flowchart showing the aerosol delivery method according to the embodiment.
Figure 7:
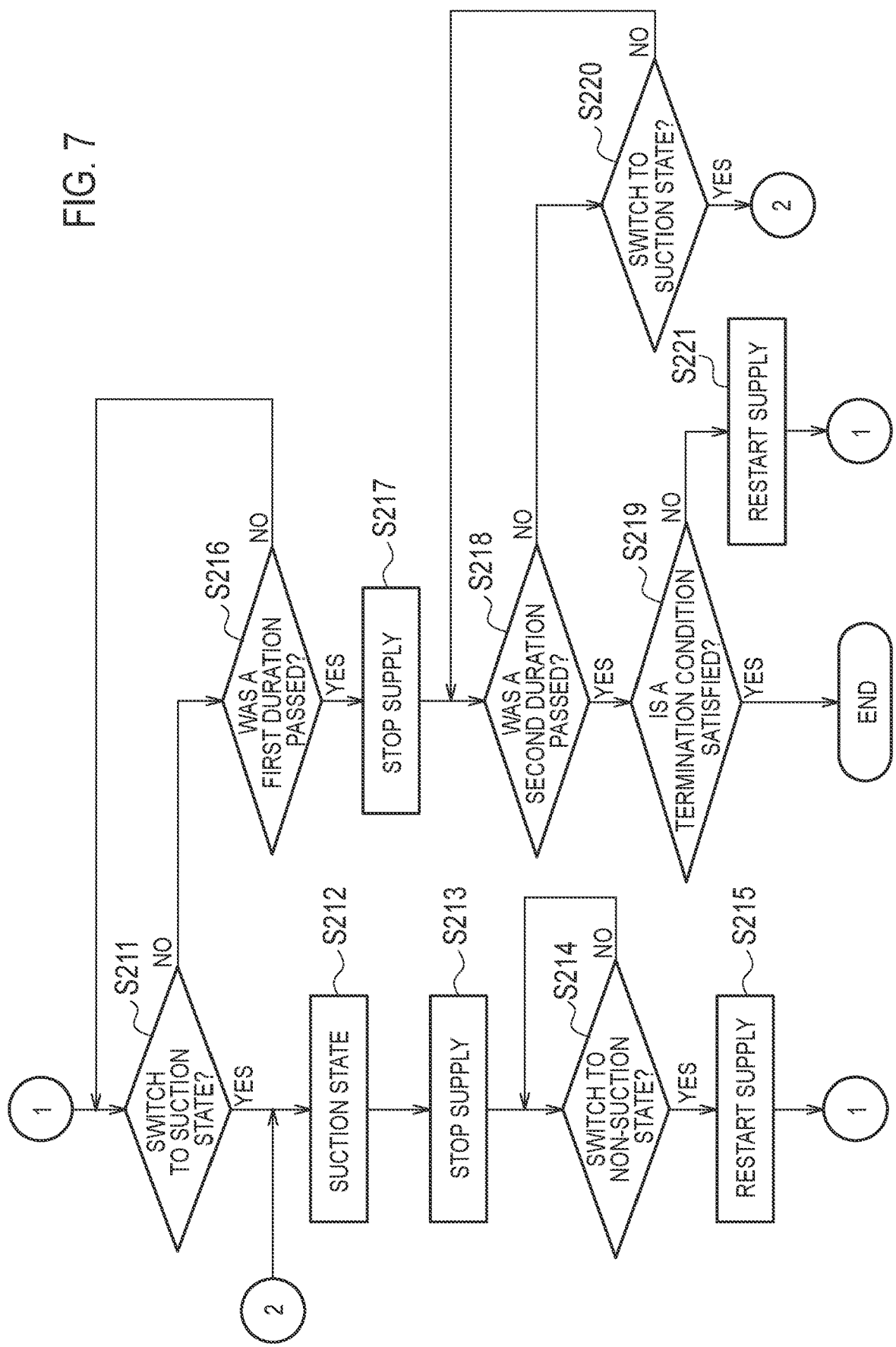
FIG. 7 is a flowchart showing the aerosol delivery method according to the embodiment.

Hereinafter, an aerosol delivery method according to the embodiment will be described. FIGS. 5 to 7 are flowcharts showing the aerosol delivery method according to the embodiment. In FIGS. 5 to 7, an operation of the flavor inhaler 100 (controller 53) will mainly be described.

As shown in FIG. 5, in step S10, the flavor inhaler 100 is powered on. For example, when the pushbutton 30 is continuously pushed in for a predetermined number of times, the flavor inhaler 100 is powered on.

In step S20, the controller 53 controls the power output associated with a puffing action. Details of step S20 will be described later (see FIGS. 6 and 7).

In step S30, the flavor inhaler 100 is powered off For example, when the pushbutton 30 is continuously pushed in for a predetermined number of times, the flavor inhaler 100 is powered off Alternatively, the flavor inhaler 100 may be powered off when a predetermined time elapses without a puffing action after a puffing action is performed.

Next, details of step S20 mentioned above will be described. FIG. 6 is a flowchart showing the aerosol delivery method in an initial puffing action. As shown in FIG. 6, in step S201, the flavor inhaler 100 is in the non-suction state where no puffing action is detected by the suction sensor 20.

In step 5202, the controller 53 determines whether the non-suction state has been switched to the suction state. In other words, the controller 53 determines whether the atomization switch 52 has been switched from the ON state to the OFF state. When the determination result is YES, the controller 53 proceeds to processing of step S203. When the determination result is NO, the controller 53 returns to processing of step S201.

In step S203, the controller 53 determines whether the suction state has been switched to the non-suction state. In other words, the controller 53 determines whether the atomization switch 52 has been switched from the OFF state to the ON state. When the determination result is YES, the controller 53 proceeds to processing of step S204. When the determination result is NO, the controller 53 waits as it is.

In step S204, the controller 53 determines whether the non-suction state has been switched to the suction state, and the suction state has been switched to the non-suction state within the trigger time. That is, the controller 53 determines whether a time from a timing of switching to the suction state to a timing of switching to the non-suction state is within the trigger time. When the determination result is YES, the controller 53 proceeds to processing of step S205. When the determination result is NO, the controller 53 returns to the processing of step S201. However, the processing of step S204 may be omitted.

In step S205, the controller 53 triggers the energization processing for the atomizer 111R. That is, after the initial puffing action detected in steps S202 and S203 is performed, the controller 53 starts supply of the power output to the atomizer 111R. In addition, the initial puffing action may be used to authenticate whether the user is an authorized user. The initial puffing action may be an initial puffing action after the flavor inhaler 100 is powered on, or may be an initial puffing action after a predetermined time has elapsed without a puffing action performed. The predetermined time is longer than at least the first duration and the second duration.

Here, the controller 53 may control the light-emitting element 40 to notify that a desired amount of aerosol cannot be supplied, after starting of supply of the power output to the atomizer 111R until the supply amount of aerosol reaches the lower limit of the desired amount range. On the other hand, when the supply amount of aerosol generated by the atomizer 111R exceeds the lower limit of the desired amount range, the controller 53 may control the light-emitting element 40 to notify that the desired amount of aerosol can be supplied. The light-emitting element 40 may continuously notify that the desired amount of aerosol can be supplied, from start to end of a period in which the desired amount of aerosol can be supplied.

After the processing of step S205, the controller 53 proceeds to processing of step S211 shown in FIG. 7. FIG. 7 is a flowchart showing the aerosol delivery method in a puffing action after the authentication (e.g., second and subsequent puffing actions).

As shown in FIG. 7, in step S211, the controller 53 determines whether the non-suction state has been switched to the suction state. In other words, the controller 53 determines whether the atomization switch 52 has been switched from the ON state to the OFF state. When the determination result is YES, the controller 53 proceeds to processing of step S212. When the determination result is NO, the controller 53 proceeds to processing of step S216.

In step S212, the flavor inhaler 100 is in the suction state where a puffing action is detected by the suction sensor 20.

In step S213, the controller 53 stops the supply of the power output to the atomizer 111R.

In step S214, it is determined whether the suction state has been switched to the non-suction state. In other words, the controller 53 determines whether the atomization switch 52 has been switched from the OFF state to the ON state. When the determination result is YES, the controller 53 proceeds to processing of step S215. When the determination result is NO, the controller 53 waits until the suction state ends.

In step S215, the controller 53 restarts the supply of the power output to the atomizer 111R. Here, until the supply amount of aerosol generated by the atomizer 111R exceeds the lower limit of the desired amount range, the controller 53 may control the light-emitting element 40 to notify that the desired amount of aerosol cannot be supplied. When the supply amount of aerosol generated by the atomizer 111R exceeds the lower limit of the desired amount range, the controller 53 may control the light-emitting element 40 to notify that the desired amount of aerosol can be supplied. After step S215, the controller 53 returns to the processing of step S211.

In step S216, the controller 53 determines whether the first duration has elapsed after starting of supply of the power output to the atomizer 111R. As described above, the first duration is the time determined to prevent the supply amount of aerosol from exceeding the upper limit of the desired amount range. When the determination result is YES, the controller 53 proceeds to processing of step S217. When the determination result is NO, the controller 53 returns to the processing of step S211.

In step S217, the controller 53 stops the supply of the power output to the atomizer 111R. Here, when the supply amount of aerosol generated by the atomizer 111R falls below the lower limit of the desired amount range, the controller 53 may control the light-emitting element 40 to notify that the desired amount of aerosol cannot be supplied. The light-emitting element 40 may continuously notify that the desired amount of aerosol cannot be supplied, from start to end of a period in which the desired amount of aerosol cannot be supplied.

Figure 4:
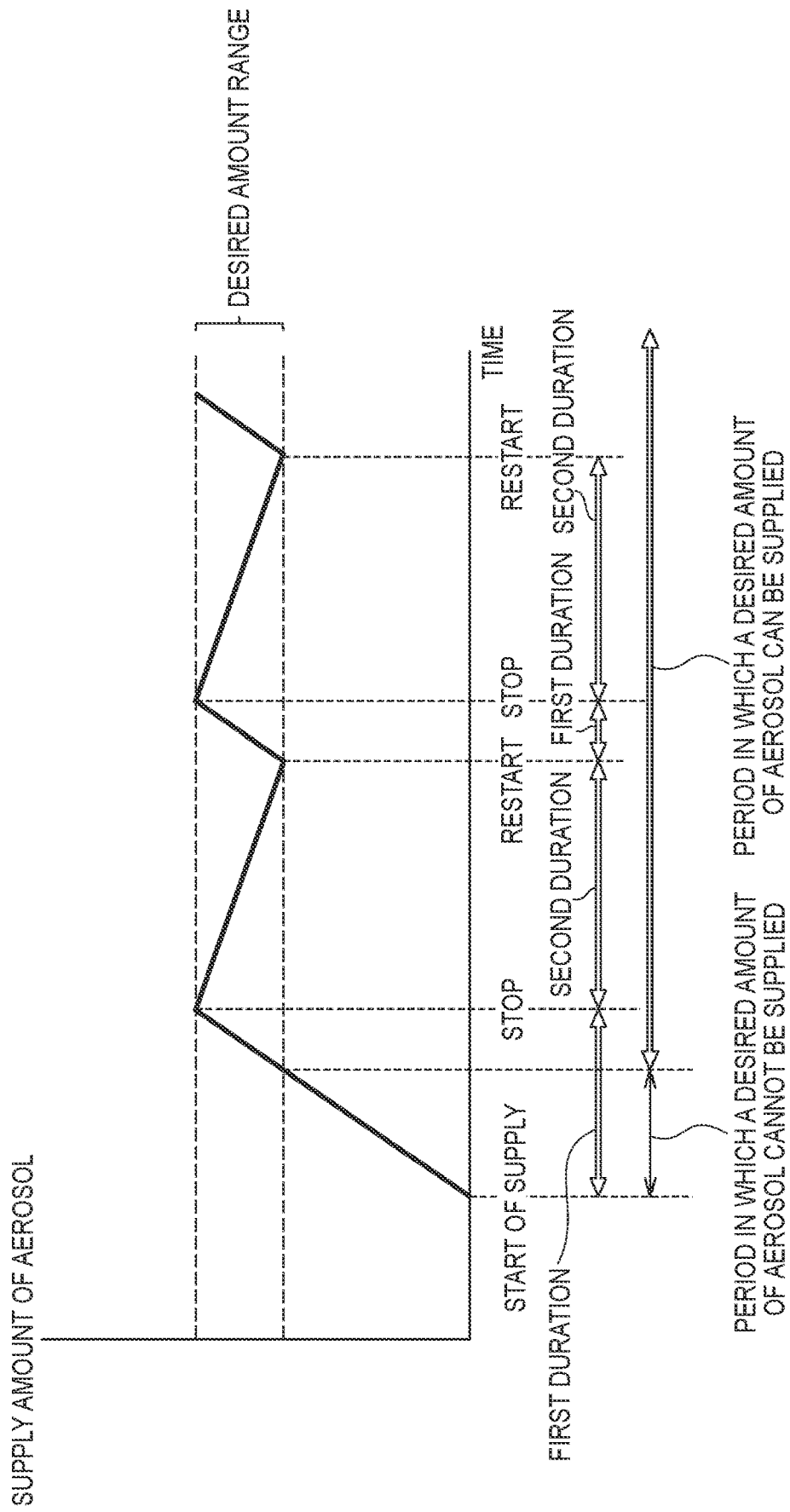
FIG. 4 is a graph for explaining an example of control of a power output to an atomizer 111R according to the embodiment.

However, it should be noted that, as in the example of control shown in FIG. 4, when the supply amount of aerosol increases or decreases within the desired amount range after the supply amount of aerosol exceeds the lower limit of the desired amount range, a state is maintained where the supply amount of aerosol is above the lower limit of the desired amount range. Therefore, it is unnecessary to notify in step S217 that the desired amount of aerosol cannot be supplied.

In step S218, the controller 53 determines whether the second duration has elapsed after stopping of supply of the power output to the atomizer 111R due to elapse of the first duration. As described above, the second duration is the time determined to prevent the supply amount of aerosol from falling below the lower limit of the desired amount range. When the determination result is YES, the controller 53 proceeds to processing of step S219. When the determination result is NO, the controller 53 proceeds to processing of step S220.

In step S219, the controller 53 determines whether a termination condition is satisfied. When the determination result is YES, the controller 53 ends a series of processing. When the determination result is NO, the controller 53 returns to processing of step S221. The termination condition may be that a predetermined time elapses without a puffing action performed, or may be that a predetermined number of puffing actions have been performed.

In step S220, the controller 53 determines whether the non-suction state has been switched to the suction state. In other words, the controller 53 determines whether the atomization switch 52 has been switched from the ON state to the OFF state. When the determination result is YES, the controller 53 proceeds to the processing of step S212. When the determination result is NO, the controller 53 returns to processing of step S218.

In step S221, the controller 53 restarts the supply of the power output to the atomizer 111R. Here, as with step S205, when the supply amount of aerosol generated by the atomizer 111R exceeds the lower limit of the desired amount range, the controller 53 may control the light-emitting element 40 to notify that the desired amount of aerosol can be supplied. The light-emitting element 40 may continuously notify that the desired amount of aerosol can be supplied, from start to end of a period in which the desired amount of aerosol can be supplied.

However, it should be noted that, as in the example of control shown in FIG. 4, when the supply amount of aerosol increases or decreases within the desired amount range after the supply amount of aerosol exceeds the lower limit of the desired amount range, a state is maintained where the supply amount of aerosol is above the lower limit of the desired amount range. Therefore, when it is notified only once that the desired amount of aerosol can be supplied at a timing when the supply amount of aerosol generated by the atomizer 111R exceeds the lower limit of the desired amount range, it is not necessary to notify that the desired amount of aerosol can be supplied in step S215. After step S221, the controller 53 returns to the processing of step S211.

As described above, the aerosol delivery method includes various processing, but the embodiment is not limited to this. The aerosol delivery method only needs to include at least step A (i.e., step S205, step S215, and step S221) of generating aerosol in the suction path, and step B (i.e., step S213) of transferring the aerosol into a user's mouth with a fluid flow in the suction path in a state where generation of aerosol is stopped after step A.

(Function and Effect)

In the embodiment, the controller 53 stops supply of the power output to the atomizer 111R during a user's puffing action. During generation of aerosol by the atomizer 111R, temperature of the atomizer 111R is not changed by the user's puffing action. This prevents a particle diameter of particles constituting aerosol from varying within one puffing action or among a plurality of puffing actions.

In the embodiment, when the first duration has elapsed after starting of supply of the power output to the atomizer 111R, the controller 53 stops the supply of the power output to the atomizer 111R. Therefore, it is possible to keep the supply amount of aerosol within a desired amount without depending on an interval of puffing actions.

In the embodiment, when the second duration has elapsed after stopping of supply of the power output to the atomizer 111R due to elapse of the first duration, the controller 53 restarts the supply of the power output to the atomizer 111R. This can prevent the supply amount of aerosol from falling below the lower limit of the desired amount range due to condensation of the aerosol on the wall surface exposed to the flow path of aerosol.

In the embodiment, the light-emitting element 40 notifies that a desired amount of aerosol can be supplied, in a period in which the desired amount of aerosol can be supplied. This allows a user to promote start of a puffing action at an appropriate timing.

In the embodiment, the light-emitting element 40 notifies that a desired amount of aerosol cannot be supplied, in a period in which the desired amount of aerosol cannot be supplied. This can prevent start of a puffing action at an inappropriate timing.

In the embodiment, on the wall surface exposed to the flow path of aerosol generated by the atomizer 111R, there is provided the absorbing member 111S that absorbs the condensed aerosol. This can suppresses waste of the aerosol source by re-atomization of the aerosol absorbed by the absorbing member 111S.

In the embodiment, the controller 53 triggers the energization processing for the atomizer 111R when the non-suction state is switched to the suction state, and the suction state is switched to the non-suction state. This makes it possible to properly trigger the energization processing for the atomizer 111R. Furthermore, an initial puffing action can be used for user authentication.

Modified Example 1

Hereinafter, Modified Example 1 of the embodiment will be described. In the following, differences from the embodiment will be mainly described.

Figure 8:
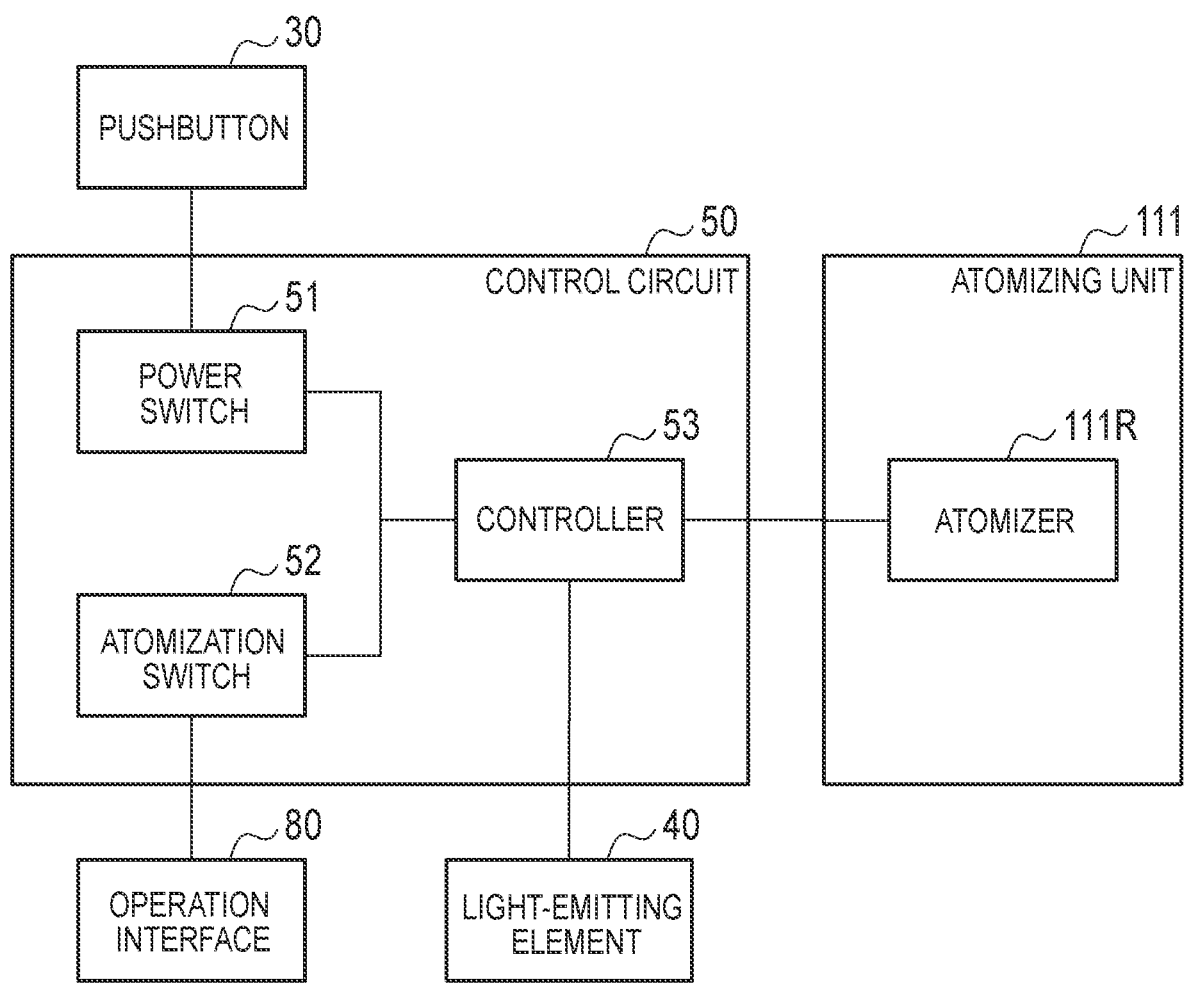
FIG. 8 is a diagram showing a block configuration of a flavor inhaler 100 according to Modified Example 1.

Specifically, in the embodiment, the atomization switch 52 is linked with the suction sensor 20. On the other hand, in Modified Example 1, an atomization switch 52 is connected to an operation interface 80 as shown in FIG. 8, and is linked with a user operation on the operation interface 80. The operation interface 80 may be the above-described pushbutton 30, or may be an interface provided separately from the pushbutton 30 described above.

The operation interface 80 is an interface configured to be operated before start of a puffing action. That is, a user operates the operation interface 80 in a period in which a puffing action is not performed, and the user does not operate the operation interface 80 in a period in which the puffing action is performed. Therefore, the atomization switch 52 is switched to an OFF state when the user operation is no longer performed on the operation interface 80. On the other hand, the atomization switch 52 is switched to an ON state when the user operation is performed on the operation interface 80. That is, a state where the user operation is being performed on the operation interface 80 is a non-suction state, and a state where the user operation is not being performed on the operation interface 80 is a suction state.

In Modified Example 1, a controller 53 starts supply of a power output to an atomizer 111R when a user operation is performed on the operation interface 80, and the controller 53 stops the supply of the power output to the atomizer 111R when the user operation is no longer performed on the operation interface 80.

Here, in a case where the control according to the embodiment is applied to Modified Example 1, "when a puffing action is detected by the suction sensor 20" may be replaced with "when a user operation is no longer performed on the operation interface 80", and "when a puffing action is no longer detected by the suction sensor 20" may be replaced with "when a user operation is performed on the operation interface 80".

On an assumption of such replacement, in Modified Example 1, step A (step S205, step 213, and step 219 described above) of generating aerosol in the suction path is a step of starting supply of the power output to the atomizer 111R when a user operation is performed on the operation interface 80, whereas step B of transferring the aerosol into a user's mouth with a fluid flow in the suction path, in a state where the generation of aerosol is stopped after step A is a step of stopping the supply of the power output to the atomizer 111R when the user operation is no longer performed on the operation interface 80.

(Example of Control)

Figure 9:
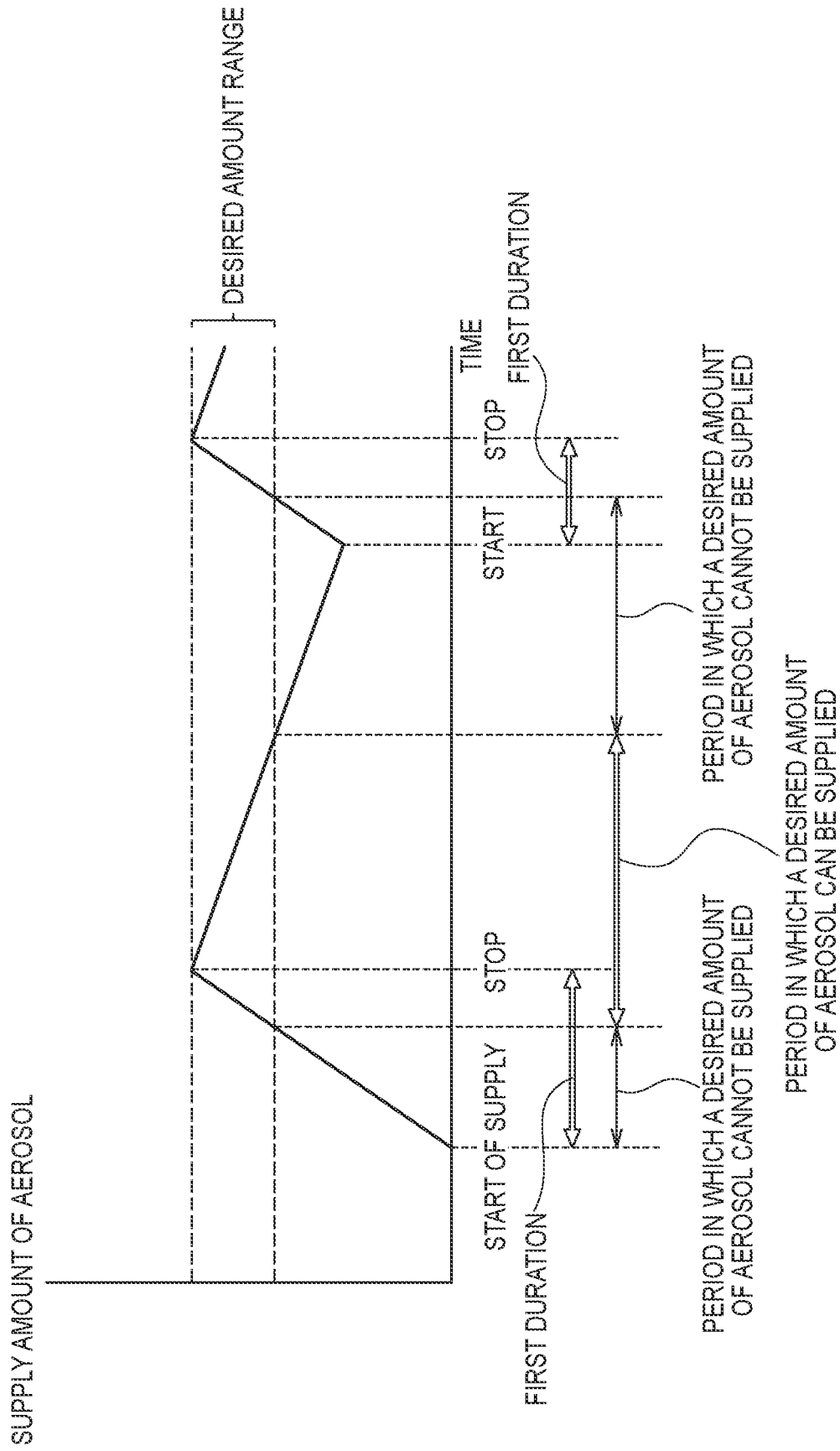
FIG. 9 is a graph for explaining an example of control of a power output to an atomizer 111R according to Modified Example 1.

Hereinafter, an example of control of the power output to the atomizer 111R according to Modified Example 1 will be described. FIG. 9 is a diagram for explaining an example of control of the power output to the atomizer 111R according to Modified Example 1.

As described above, when a user operation is performed on the operation interface 80, the controller 53 starts supply of the power output to the atomizer 111R. When the user operation is not being performed on the operation interface 80, the controller 53 stops supply of the power output to the atomizer 111R.

In such a case, as shown in FIG. 9, the controller 53 stops the supply of the power output to the atomizer 111R when the first duration elapses with the atomization switch 52 being in the ON state (i.e., the non-suction state) after starting of supply of the power output to the atomizer 111R. That is, even when the user operation is continued on the operation interface 80, the supply of the power output to the atomizer 111R is stopped. The first duration is the time determined to prevent the supply amount of aerosol from exceeding an upper limit of the desired amount range. However, the example of control according to Modified Example 1 does not include performing of the control for maintaining the supply amount of aerosol to exceed a lower limit of the desired amount range by using the second duration described above.

Here, the controller 53 controls the light-emitting element 40 to notify that the desired amount of aerosol can be supplied. Further, the controller 53 controls the light-emitting element 40 to notify that the desired amount of aerosol cannot be supplied. In the example of control according to Modified Example 1, when the supply amount of aerosol is below the lower limit of the desired amount range, it is notified that the desired amount of aerosol cannot be supplied. When the supply amount of aerosol is above the lower limit of the desired amount range, it is notified that the desired amount of aerosol can be supplied.

(Function and Effect)

In Modified Example 1, even when the operation interface 80 is used instead of the suction sensor 20, similar effects to the embodiment can be obtained. Further, as a result of omitting the control for maintaining the supply amount of aerosol to exceed the lower limit of the desired amount range by using the second duration described above, power consumption and a processing load are reduced as compared with the embodiment.

Modified Example 2

Hereinafter, Modified Example 2 of the embodiment will be described. In the following, differences from the embodiment will be mainly described.

Figure 10:
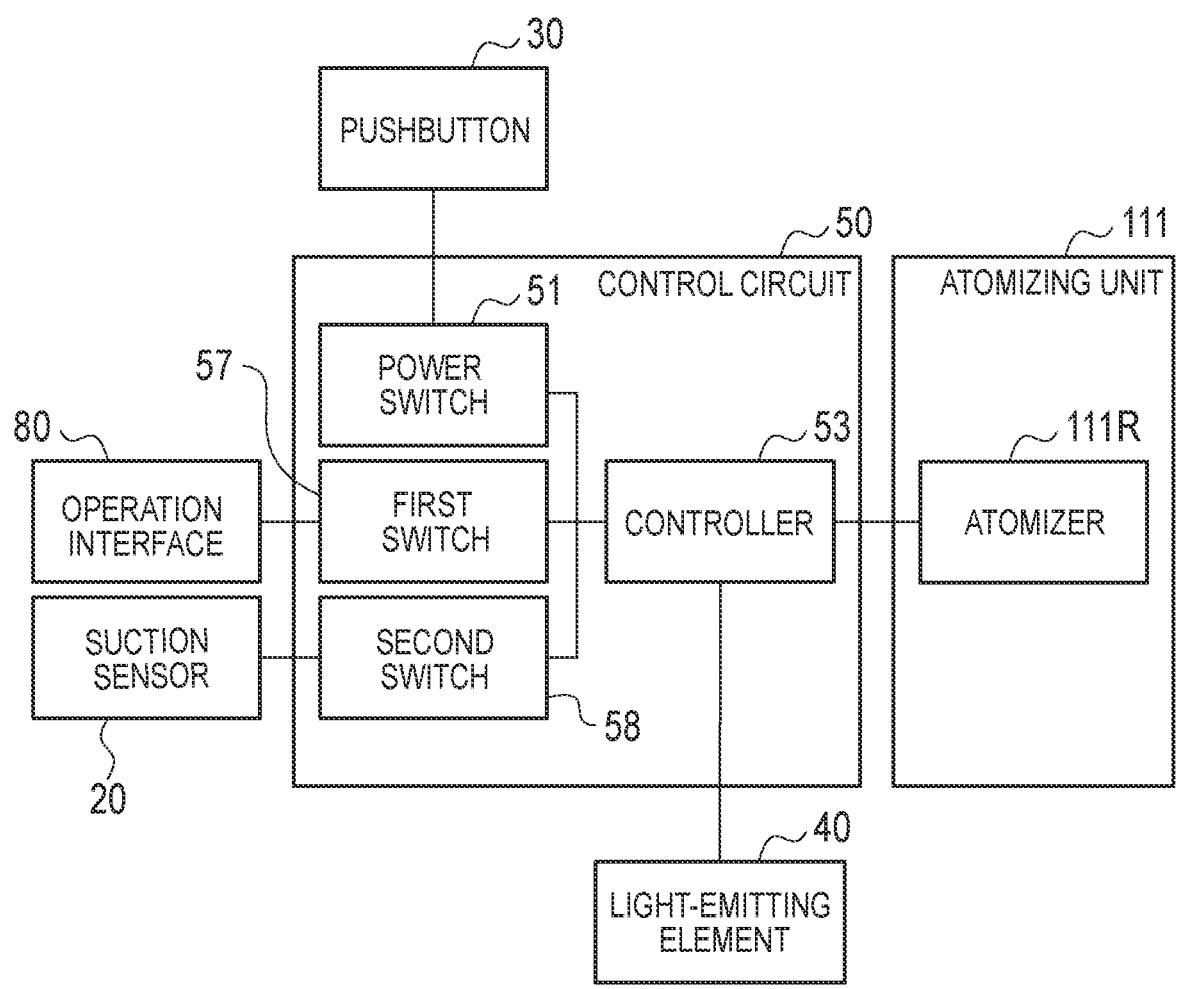
FIG. 10 is a diagram showing a block configuration of a flavor inhaler 100 according to Modified Example 2.

In the embodiment, there is provided the atomization switch 52 linked with the suction sensor 20. On the other hand, in Modified Example 2, as shown in FIG. 10, there are provided a first switch 57 linked with an operation interface 80, and a second switch 58 linked with a suction sensor 20. The operation interface 80 may be the above-described pushbutton 30, or may be an interface provided separately from the pushbutton 30 described above.

In Modified Example 2, the first switch 57 is switched to an ON state when a user operation is performed on the operation interface 80, and is switched to an OFF state when the user operation is no longer performed on the operation interface 80. On the other hand, the second switch 58 is switched to an ON state when a puffing action is detected by the suction sensor 20, and is switched to an OFF state when the puffing action is no longer detected by the suction sensor 20. That is, the second switch 58 is switched to the ON state by start of a user's puffing action, and switched to the OFF state by termination of the user's puffing action.

In Modified Example 2, when the first switch 57 is switched to the ON state, a controller 53 starts supply of the power output to an atomizer 111R, and when the second switch 58 is switched to the ON state, the controller 53 stops the supply of the power output to the atomizer 111R. In other words, the controller 53 starts supply of the power output to the atomizer 111R when a user operation is performed on the operation interface 80, and even when the user operation is being performed on the operation interface 80, the controller 53 stops the supply of the power output to the atomizer 111R when a puffing action is detected by the suction sensor 20.

Thus, it should be noted that, in Modified Example 2, an opportunity to start supply of the power output to the atomizer 111R is that a user operation is performed on the operation interface 80 (the first switch 57 is switched to the ON state), rather than that a puffing action is no longer detected by the suction sensor 20 (the second switch 58 is switched to the OFF state).

In Modified Example 2, the operation interface 80 is used as an interface to start supply of the power output to the atomizer 111R. Therefore, when the user operation is no longer performed on the operation interface 80, the controller 53 may not stop the supply of the power output to the atomizer 111R. However, Modified Example 2 is not limited to this. Specifically, when the user operation is no longer performed on the operation interface 80, the controller 53 may stop the supply of the power output to the atomizer 111R. Specifically, on the assumption that the user operation is being performed on the operation interface 80 (i.e., the first switch 57 is in the ON state), it may be considered that supply of the power output to the atomizer 111R is permitted.

It should be noted that, in Modified Example 2, the control shown in FIG. 9 is performed as control of the power output to the atomizer 111R, as in Modified Example 1. That is, Modified Example 2 does not include performing of the control for maintaining the supply amount of aerosol to exceed the lower limit of the desired amount range by using the second duration described above.

In Modified Example 2, from a viewpoint of stopping supply of the power output to the atomizer 111R, the second switch 58 linked with the suction sensor 20 may be considered as an atomization switch. From a viewpoint of starting supply of the power output to the atomizer 111R, the first switch 57 linked with the operation interface 80 may be considered as the atomization switch.

(Aerosol Delivery Method)

Figure 11:
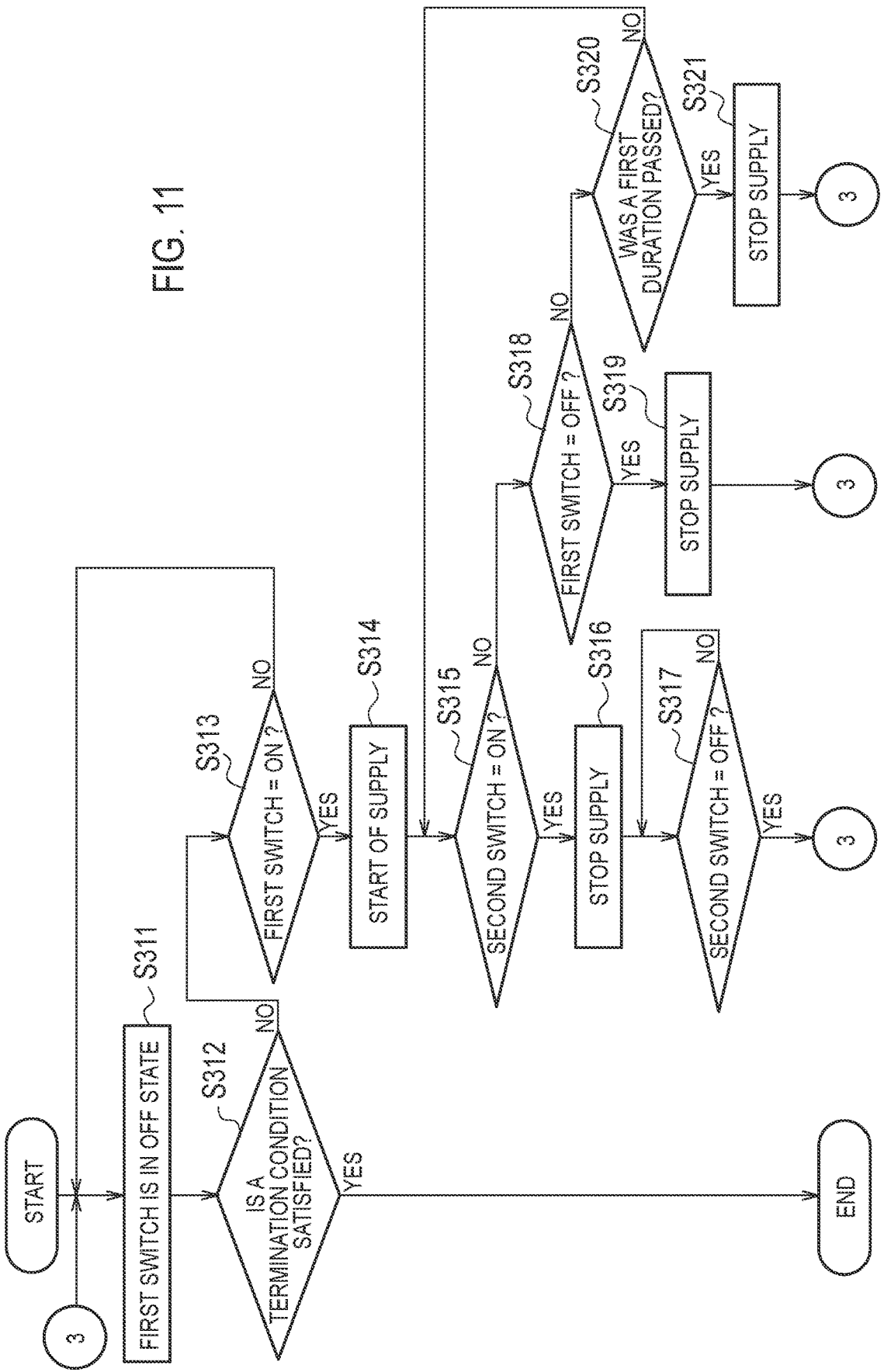
FIG. 11 is a flowchart showing an aerosol delivery method according to Modified Example 2.

Hereinafter, an aerosol delivery method according to Modified Example 2 will be described. FIG. 11 is a flowchart showing the aerosol delivery method according to Modified Example 2. In FIG. 11, an operation of the flavor inhaler 100 (controller 53) is mainly described. In FIG. 11, details of step S20 shown in FIG. 5 is described.

As shown in FIG. 11, in step S311, the first switch 57 is in the OFF state. That is, a user operation is not being performed on the operation interface 80.

In step S312, the controller 53 determines whether a termination condition is satisfied. When the determination result is YES, the controller 53 ends a series of processing. When the determination result is NO, the controller 53 returns to processing of step S313. The termination condition may be that a predetermined time elapses without a puffing action performed, or may be that a predetermined number of puffing actions have been performed.

In step S313, the controller 53 determines whether the first switch 57 has been switched from the OFF state to the ON state. In other words, the controller 53 determines whether a user operation has been performed on the operation interface 80. When the determination result is YES, the controller 53 proceeds to processing of step S314. When the determination result is NO, the controller 53 returns to processing of step S311.

In step S314, the controller 53 starts supply of the power output to the atomizer 111R. Here, when the supply amount of aerosol generated by the atomizer 111R exceeds a lower limit of a desired amount range, the controller 53 may control the light-emitting element 40 to notify that the desired amount of aerosol can be supplied.

In step S315, the controller 53 determines whether the second switch 58 has been switched from the OFF state to the ON state. In other words, the controller 53 detects whether a puffing action is detected by the suction sensor 20. When the determination result is YES, the controller 53 proceeds to processing of step S316. When the determination result is NO, the controller 53 returns to processing of step S318.

In step S316, the controller 53 stops the supply of the power output to the atomizer 111R.

In step S317, the controller 53 determines whether the second switch 58 has been switched from the ON state to the OFF state. In other words, the controller 53 detects whether the puffing action is no longer detected by the suction sensor 20. When the determination result is YES, the controller 53 returns to the processing of step S311. In the flow shown in FIG. 11, the first switch 57 is switched from the ON state to the OFF state even when the user operation is continued on the operation interface 80 at a time of returning to processing at step S311. On the other hand, when the determination result is NO, the controller 53 waits as it is. In other words, it should be noted that, since the next step is not processed when the second switch 58 in the ON state due to the detection of a user's puffing action, the power output to the atomizer 111R is not started even when the first switch 57 is turned on by the user operation on the operation interface 80.

In step S318, it is determined whether the first switch 57 has been switched from the ON state to the OFF state. In other words, the controller 53 determines whether the user operation is no longer performed on the operation interface 80. When the determination result is YES, the controller 53 proceeds to processing of step S319. When the determination result is NO, the controller 53 returns to processing of step S320.

In step S319, the controller 53 stops the supply of the power output to the atomizer 111R. Here, when the supply amount of aerosol generated by the atomizer 111R falls below the lower limit of the desired amount range, the controller 53 may control the light-emitting element 40 to notify that the desired amount of aerosol cannot be supplied. After step S319, the controller 53 returns to the processing of step S311.

In step S320, the controller 53 determines whether the first duration has elapsed after starting of supply of the power output to the atomizer 111R. As described above, the first duration is the time determined to prevent the supply amount of aerosol from exceeding the upper limit of the desired amount range. When the determination result is YES, the controller 53 proceeds to processing of step S321. When the determination result is NO, the controller 53 returns to processing of step S315.

In step S321, the controller 53 stops the supply of the power output to the atomizer 111R. Here, when the supply amount of aerosol generated by the atomizer 111R falls below the lower limit of the desired amount range, the controller 53 may control the light-emitting element 40 to notify that the desired amount of aerosol cannot be supplied. After step S321, the controller 53 returns to the processing of step S311. In the flow shown in FIG. 11, the first switch 57 is switched from the ON state to the OFF state even when the user operation is continued on the operation interface 80 at a time of returning to processing at step S311.

(Function and Effect)

In Modified Example 2, even when the first switch 57 and the second switch 58 are used instead of the atomization switch 52, similar effects to the embodiment can be obtained. Further, as a result of omitting the control for maintaining the supply amount of aerosol to exceed the lower limit of the desired amount range by using the second duration described above, power consumption and a processing load are reduced as compared with the embodiment.

[Other Embodiments]

Although the present invention has been described with the above-described embodiments, the descriptions and drawings forming a part of the disclosure should not be construed as limiting the present invention. From this disclosure, various alternative embodiments, examples, and operation techniques will be apparent to those skilled in the art.

In the embodiment, the cartridge 130 does not include the atomizing unit 111, but the embodiment is not limited to this. For example, the cartridge 130 may form one unit in combination with the atomizing unit 111.

In the embodiment, the flavor inhaler 100 has the cartridge 130, but the embodiment is not limited to this. The flavor inhaler 100 may not have the cartridge 130. In such a case, the aerosol source preferably contains a flavoring component.

In the embodiment, the flavor inhaler 100 has the power switch 51, but the embodiment is not limited to this. In other words, the suction sensor 20 may always be energized.

The pushbutton 30 is provided at the non-inhalation end of the flavor inhaler 100, but the embodiment is not limited to this. For example, the pushbutton 30 may be provided on an outer periphery of the inhaler housing 110X.

As shown in FIG. 9, Modified Examples 1 and 2 do not include performing of the control by using the second duration, that is, the control for maintaining the supply amount of aerosol to exceed the lower limit of the desired amount range, but the embodiment is not limited to this. Even in Modified Examples 1 and 2, the control using the second duration period may be performed as shown in FIG. 4. In detail, after stopping of the supply of the power output to the atomizer 111R due to elapse of the first duration, the controller 53 according to Modified Example 1 may restart the supply of the power output to the atomizer 111R when the second duration has elapsed with the atomization switch 52 being in the ON state (i.e., while the user operation is performed on the operation interface 80). After stopping of the supply of the power output to the atomizer 111R due to elapse of the first duration, the controller 53 according to Modified Example 2 may restart the supply of the power output to the atomizer 111R when the second duration has elapsed with the first switch 57 being in the ON state, and the second switch 58 being in the OFF state (i.e., while the user operation is continued on the operation interface 80, and no puffing action is being detected by the suction sensor 20).

Although not specifically mentioned in the embodiment, the atomizing unit 111 may be provided separately from the electrical unit 112, and may be configured to be connectable to the electrical unit 112.

INDUSTRIAL APPLICABILITY

According to the embodiment, it is possible to provide the non-combustion type flavor inhaler and the aerosol delivery method capable of suppressing variations in the particle diameter of the particles constituting the aerosol.

The invention claimed is:

1. A non-combustion type flavor inhaler comprising:
an atomizer atomizing an aerosol source without burning; and
a controller controlling supply of a power output to the atomizer so that aerosol can be supplied to a user during a predetermined time, wherein
the controller is configured, in response to a user's puffing action during the predetermined time, to stop supply of a power output to the atomizer for the remainder of that puffing action, and then, in response to the end of that puffing action, to start the supply of a power output to the atomizer so that an amount of aerosol generated by the atomizer does not fall below a predetermined lower limit,
wherein during generation of the aerosol by the atomizer, a temperature of the atomizer is not changed by the user's puffing action, wherein a particle diameter of particles constituting aerosol is maintained between a plurality of puffing actions.

2. The non-combustion type flavor inhaler according to claim 1, further comprising an atomization switch that is switched to a state where supply of a power output to the atomizer is stopped when a user's puffing action is performed.

3. The non-combustion type flavor inhaler according to claim 2, wherein the atomization switch is switched to a state where supply of a power output to the atomizer is started when a user's puffing action is no longer performed.

4. The non-combustion type flavor inhaler according to claim 2, wherein the atomization switch is linked with a suction sensor that detects a puffing action, and
the controller stops supply of a power output to the atomizer when a puffing action is detected by the suction sensor.

5. The non-combustion type flavor inhaler according to claim 2, wherein the atomization switch is linked with a suction sensor that detects a puffing action, and
the controller starts supply of a power output to the atomizer when a puffing action is no longer detected by the suction sensor.

6. The non-combustion type flavor inhaler according to claim 2, wherein the atomization switch is linked with a user operation on an operation interface, and
the controller stops supply of a power output to the atomizer when a user operation is no longer performed on the operation interface.

7. The non-combustion type flavor inhaler according to claim 2, wherein the atomization switch is linked with a user operation on an operation interface, and
the controller starts supply of a power output to the atomizer when a user operation is performed on the operation interface.

8. The non-combustion type flavor inhaler according to claim 1, further comprising:
a first switch that is switched to an ON state when a user operation is being performed on an operation interface, and that is switched to an OFF state when a user operation is not being performed on the operation interface; and
a second switch that is switched to an ON state by start of a user's puffing action, and is switched to an OFF state by termination of a user's puffing action, wherein
the controller starts supply of a power output to the atomizer when the first switch is switched to the ON state, and the controller stops supply of a power output to the atomizer when the second switch is switched to the ON state.

9. The non-combustion type flavor inhaler according to claim 1, wherein the controller stops supply of a power output to the atomizer when a first duration has elapsed after starting of supply of a power output to the atomizer.

10. The non-combustion type flavor inhaler according to claim 9, wherein the controller restarts supply of a power output to the atomizer when a second duration has elapsed after stopping of the supply of a power output to the atomizer due to the elapse of the first duration.

11. The non-combustion type flavor inhaler according to claim 1, further comprising: a notification unit that notifies that a desired amount of aerosol can be supplied, in a period in which the desired amount of aerosol can be supplied.

12. The non-combustion type flavor inhaler according to claim 1, further comprising: a notification unit that notifies that a desired amount of aerosol cannot be supplied in a period in which the desired amount of aerosol cannot be supplied.

13. The non-combustion type flavor inhaler according to claim 1, wherein an absorbing member for absorbing a condensed aerosol is provided on a wall surface exposed to a flow path of aerosol generated by the atomizer.

14. The non-combustion type flavor inhaler according to claim 1, further comprising:
a suction sensor that detects a puffing action, wherein
the controller triggers energization processing for the atomizer when switching is performed from a non-suction state in which a puffing action is not detected by the suction sensor, to a suction state in which a puffing action is detected by the suction sensor, and from the suction state to the non-suction state.

15. The non-combustion type flavor inhaler according to claim 1, wherein
the controller is configured to supply a power output to the atomizer during periods other than periods in which user's puffing action is being detected.

16. The non-combustion type flavor inhaler according to claim 15, wherein
the controller is configured to stop supply of a power output to the atomizer when a predetermined duration has lapsed without a new user's puffing action being detected since the end of the latest user's puffing action.

* * * * *